US009504722B2

(12) United States Patent
Gokaraju et al.

(10) Patent No.: US 9,504,722 B2
(45) Date of Patent: *Nov. 29, 2016

(54) ANTI-OBESE COMPOSITIONS CONTAINING HOLOPTELEA INTEGRIFOLIA EXTRACTS

(75) Inventors: Ganga Raju Gokaraju, Vijayawada (IN); Rama Raju Gokaraju, Vijayawada (IN); Trimurtulu Golakoti, Vijayawada (IN); Krishanu Sengupta, Vijayawada (IN); Kiran Bhupatiraju, Vijayawada (IN)

(73) Assignee: Laila Nutraceuticals, Vijayawada (IN)

( * ) Notice: Subject to any disclaimer, the term of this patent is extended or adjusted under 35 U.S.C. 154(b) by 473 days.

This patent is subject to a terminal disclaimer.

(21) Appl. No.: 12/674,113

(22) PCT Filed: Aug. 20, 2007

(86) PCT No.: PCT/IN2007/000356
§ 371 (c)(1),
(2), (4) Date: Feb. 18, 2010

(87) PCT Pub. No.: WO2009/024991
PCT Pub. Date: Feb. 26, 2009

(65) Prior Publication Data
US 2010/0203078 A1 Aug. 12, 2010

(51) Int. Cl.
*A61K 36/185* (2006.01)
(52) U.S. Cl.
CPC .................................. *A61K 36/185* (2013.01)
(58) Field of Classification Search
None
See application file for complete search history.

(56) References Cited

U.S. PATENT DOCUMENTS

2005/0130933 A1* 6/2005 Jacobs et al. ................... 514/54

OTHER PUBLICATIONS

Parinitha et al. Ethnobotanical Wealth of Bhadra Wildlife Sanctuary in Karnatakata. Indian J. Traditional Knowledge. vol. 3, No. 1, p. 42. Jan. 2004.*
Cardiovascular Disease. Lab Tests Online. Retrieved from the internet. <http://labtestsonline.org/understanding/conditions/cvd/>. Retrieved on Sep. 14, 2011. 2 pages.*
Crisp et al. Adipogenesis in Thyroid Eye Disease. Invest Ophthalmol Vis Sci. 2000. 41. 3249-3255.*
Camm et al. The ESC Textbook fo Cardiovascular Medicine. Wiley-Blackwell. 2006. Page 338.*
Rosen et al. Adipocyte Differentiation from the Inside Out. Nature Reviews Molecular Cell Biology. vol. 7, Dec. 2006. pp. 885-896.*
Chai et al. Gene Regularion in B-sitosterol-mediated Stimulation of Adipogenesis, Glucose Uptake, and Lipid Mobilization in Rat Primary Adipocytes. Genes Nutr. 2011. May; 6 (2) 191-188.*
Sodhala et al. Indradeva Tripathi. part 2 (Kaya cikitsa Khanda Cahukhamba Sanskrit Sanstan (Varanasi) $3^{rd}$ Edition. 1999, p. 653, Translation.*
Anwikar et al. Study of the Synergistic Anti-Inflammatory Activity of Solanum xanthocarpum Schrad and Wendl and Cassia Fistula Linn. Int. J Ayurveda Res. 2010. Jul.-Sep. 1 (2) : 167-171. (pp. 1-7 printed).*
Sharma et al. Studies on Bionematicidal Properties of Flower and Seed Extracts of Some Plants. Proc. Nat. Acad. Sci. India. 64 (B) II, 1994. pp. 231-232.*
Mason et al. Advances in Sonochemistry. Elsevier. 1999. p. 237.*
Watanabe. Proceedings of the $3^{rd}$ International Conference on Food Factors. IOS Press. 2004. p. 195.*
goylordchemical.com Retrieved from the internet on Feb. 14, 2012. <http://www.gaylordchemical.com/index.php?page=pharmaceuticals> 3 pages.*
drugbank.ca. Retrieved from the internet on Feb. 15, 2012. <http://www.drugbank.ca/drugs/DB01093>. 6 pages.*
Pulliah. Encyclopedia of World Medicinal Plants. regency Publication. 2006. 3. p. 1095-1097.*
Rajbhandari et al. Screening of Nepalese medicinal plants of antiviral activity. Journal of Ethnopharmacology. 74, 252, 252-255.*
Lewis. Medical Botany. Plants affecting Man's Health. John Wiley & Sons. 1977. pp. 212-213.*
Trivedi et al. Vegetable Drugs Regulating Fat Metabolism in Caraka. 1972. Quart L Crude Res. 12 (24). 1988-1999.*
(W1) Longman, 0. "Holoptelea integifolia (Roxb.) Planch" from Indian Medicinal Plants a compendium of 500 species 3. 1995, p. 162.*
WHO's fact sheet No. 311, Sep. 2006, http://www.who.int/mediacentre/factsheets/fs311/en/index.html.
H. G. Preuss, et al, Efficacy of a novel, natural extract of (−)-hydroxycitric acid (HCA-SX) and a combination of HCA-SX, niacinbound chromium and Gymnema sylvestre extract in weight management in human volunteers: A pilot study. Nutrition Research, 2004, 24, 45-48.
C. A. Haller and N. L. Benowitz. Adverse cardiovascular and central nervous system events associated with dietary supplements containing ephedra alkaloids. New England J. Medicine, 2000, 343, 1833-1838.
Ziuozenkova et al., Lipolysis of triglyceride-rich lipoproteins generates PPAR ligands: Evidence for an antiinflammatory role for lipoprotein lipase. PNAS, Mar. 4, 2003, vol. 100, No. 5, 2730-2735.
Thomas, GN, the Trp64Arg polymorphism of the b3-adrenergic receptor gene and obesity in Chinese subjects with components of the metabolic syndrome. International Journal of Obesity, (2000) 24, 545-551.

(Continued)

*Primary Examiner* — Amy L Clark
(74) *Attorney, Agent, or Firm* — Kramer Amado P.C.

(57) ABSTRACT

The present invention discloses the extracts of *Holoptelea integrifolia* or the purified fractions isolated there from and the dietary, nutraceutical and pharmaceutical compositions comprising the same or optionally in combination with one or more known anti-obesic agents useful for the purpose of inhibition, amelioration or prevention of adipogenesis and lipolysis involved diseases. The invention further discloses a method for treating or preventing obesity and adipogenesis and lipolysis involved diseases using the compositions containing the extracts of purified fractions of *Holoptelea integrifolia*.

16 Claims, 2 Drawing Sheets

(56) References Cited

OTHER PUBLICATIONS

Peter Arner, The β3-Adrenergic Receptor—A Cause and Cure of Obesity? The New England Journal of Medicine, (1995) 333, 382-383.

Sodhala; Gadanigraha ed, Ganga Sahaya Pandeya & com.—Indradeva Tripathi, Part-2 (Kaya cikitsa Khanda Cahukhamba Sanskrit Sanstan (Varanasi) Ed. 3rd 1999 p. 653.

Bharata Bhaisajya Ratnakara—Compiled by Naginadasa Chaganalala Saha, Translated by Gopinath Gupta—vol. V:B Jain Publishers, New Delhi, Edn. 2nd Reprint, Aug. 1999, p. 247.

Susruta; Susruta Samhita—Edited & translated by P.V. Sharma. vol.-II: Chaukamba Visvabharati, Varanasi Edn, 1st, 2000, p. 376.

Sharma et at, "Holoptelea Integrifolea: An Overview," European Journal of Applied Sciences, vol. 4, No. 1, pp. 42-46 (2012).

Gniwotta et, al., What Do Microbes Encounter at the Plant Surface? Chemical Composition of Pea Leaf Cuticular Waxes. Plant Physiology, vol. 139, pp. 519-530 (2005).

Khmelnitsky, et al., "Relationship betweekn surface hydrophilicity of a protein and its stability against denaturation by organic solvents", FEBS Letters, vol. 284, No. 2, 267-269, 1991.

Uversky, et al., "Conformational transitions provoked by organic solvents in B-lactoglobulin: can a molten globule like intermediate be induced by the decrease in dielectric constant?", Folding & Design, Apr. 24, 1997, vol. 2, No. 3, pp. 163-172.

* cited by examiner

ANTI-OBESE COMPOSITIONS CONTAINING HOLOPTELEA INTEGRIFOLIA EXTRACTS

TECHNICAL FIELD OF INVENTION

The present invention relates to an extract of *Holoptelea integrifolia*, more specifically the purified fraction isolated therefrom having anti-adipogenic and pro-lipolysis activities for the purpose of inhibition, amelioration or prevention of obesity, lipid storage disease and hyperlipedemia, and the manufacturing process thereof. More particularly, the present invention relates to the compositions comprising biologically effective amount of the said extract as an active alone or optionally containing one or more of the extracts of *Hoodia*, coffee bean, *Garcinia*, green tea etc., formulated along with biologically acceptable excipients.

BACKGROUND OF THE INVENTION

Obesity is excess body weight for a particular age, sex and height as a consequence of imbalance between energy intake and energy expenditure. The primary causes of obesity are either due to overeating, inadequate exercise or eating disorder, some genetic disorders, underlying illness (e.g., hypothyroidism), certain medications, sedentary lifestyle, a high glycemic diet (i.e., a diet that consists of meals that give high post prandial blood sugar) weight cycling (caused by repeated attempts to lose weight by dieting, eating disorders), stress and insufficient sleep.

During the past 20 years, obesity among adults has risen significantly in the United States. The latest data from the National Center for Health Statistics show that 30 percent of U.S. adults of 20 years of age and older, i.e. over 60 million people, are obese. The percentage of young people, who are overweight, has more than tripled since 1980. More than 16% of the children and teens aged 6-19 years, that is over 9 million young people, are considered overweight.

Although, the US national health objectives for the year 2010 is to reduce the prevalence of obesity to less than 15% among adults, current data indicate that the situation is worsening rather than improving (http://www.cdc.gov/nchs/products/pubs/pubd/hestats/overweight/overwght_adult_03.htm). Obesity increases the risk of many diseases and health conditions such as hypertension, dyslipidemia (for example, high total cholesterol or high levels of triglycerides), type 2 diabetes, coronary heart disease, stroke, gallbladder disease, osteoarthritis, sleep disorders, respiratory problems, tumors (endometrial, breast, and colon), arteriosclerosis and heart failure.

As per World Health Organisation's latest projections, approximately 1.6 billion adults (age 15+) were overweight and at least 400 million adults were obese globally in 2005. WHO further projects that by 2015, approximately 2.3 billion adults will be overweight and more than 700 million will be obese (WHO's fact sheet No. 311, September 2006, http://www.who.int/mediacentre/factsheets/fs311/en/index.html). Obesity in Europe was recognized as a serious problem, with up to 27% of men, 38% of women and 3 million children are clinically obese (http://ec.europa.eu/health/ph_determinants/life_style/nutrition/green_papemutritiongp_co183_en.pdf). The obesity was not limited to developed countries, but it was rapidly becoming a problem in developing countries as well. The number of those affected, particularly children, are continuing to increase at an alarming rate. Obesity is already responsible for 2-8% of health care costs and 10-13% of deaths in different parts of Europe (http://www.euro.who.int/obesity).

Recent studies have shown that approximately a third of variance in adult body weights result from genetic influences. Leptin, an adipocyte and placenta-derived circulating protein, regulates the magnitude of fat stores in the body leading to obesity. Gastrointestinal peptides, neurotransmitters and adipose tissue may also have an etiologic role in obesity. Obesity and adipose tissue expansion increase the risk of hypertension, type 2 diabetes, arthritis, elevated cholesterol, cancer and serious hormonal imbalances in women, leading to sterility. Low caloric diets with or without exercise can help with temporary weight loss; however, diet and exercise alone have not proven successful for long-term solutions in weight management (H. G. Preuss, et al, Nutrition Research, 2004, 24, 45-48). In addition, supplementation with drugs that suppress appetite, reduce food intake, reduce dietary fat absorption, increase energy expenditure and effect nutrient partitioning or metabolism have potential efficacy but they are unfortunately accompanied by adverse side effects (C. A. Haller and N. L. Benowitz. Adverse cardiovascular and central nervous system events associated with dietary supplements containing ephedra alkaloids (New England J. Medicine, 2000, 343, 1833-1838). Herbal and natural products containing *Gymnema* extract, *Garcinia* extract, or carnitine are known to prevent fat accumulation through the inhibition of fat absorption, enhancement of fat decomposition, and the enhancement of fat consumption by the body.

Ever since obesity has become an epidemic, the word "diet" is gathering lot of interest from different sections of many people. Many methods for weight reduction have been introduced, which leads to disproportion of nourishment and abnormal body metabolism.

Obesity is the culmination of many underlying mechanisms. Obesity is characterized as uncontrolled adipose tissue mass in the body and recognized as the fastest growing metabolic disorder in the world. An increase in adipose tissue can be the result of the production of new fat cells through the process of adipogenesis and/or the deposition of increased amounts of cytoplasmic triglyceride or lipid droplets per cell. In the adipogenesis process, proliferation of preadipocytes or precursor fat cells needs to be followed by the differentiation of these cells to the mature adipocyte phenotype. Increased lipid accumulation in the mature adipocyte cells is the most important feature of obesity disorder. Peroxisome Proliferator-Activator Receptor gamma (PPAR-γ) is predominantly expressed in adipocytes and is a key determination factor for adipogenesis.

Fat is stored as triglycerides form in adipose tissue. The breakdown of this fat in fat cells into glycerol and fatty acids is known as lipolysis. During this process, free fatty acids are released into the bloodstream and circulate throughout the body. The hormones called epinephrine, norepinephrine, glucagon and adrenocorticotropic hormone induce lipolysis. These hormones trigger 7TM receptors, which activate adenylate cyclase. This results in increased production of cAMP, which activates protein kinase A, which subsequently activate lipases found in adipose tissue. It is known that PPAR alpha plays an important role in regulating lipolysis through the control of lipid metabolic enzymes such as lipoprotein lipase (LPL) Ziuozenkova et al., PNAS, Mar. 4, 2003, Vol. 100 no. 5, 27302735).

Inhibition of the differentiation of pre-adipocytes into mature adipocytes leads to the reduction of new adipose tissue and reduction in the formation of fat reserves. Modulation of adipogenesis and lipolysis in humans may thus lead to reduction in the burden of obesity. The body's adrenergic system plays a major part in regulating energy expenditure and lipolysis. In this process catecholamines mobilize energy-rich lipids by stimulating lipolysis in fat cells and thermogenesis in brown adipose tissue and skeletal muscle. The adrenergic receptor β3 is the principal receptor mediating catecholamine-stimulated thermogenesis in brown adipose tissue, which in humans is distributed about the great vessels in the thorax and abdomen (Thomas, G N, International Journal of Obesity, 545-551, 24, 2000). The $β_3$-adrenergic receptor is also important in mediating the stimulation of lipolysis by catecholamines in the white fat cells of several species, including humans. The brown adipose tissue differs from white adipose tissue in that it has large numbers of mitochondria containing a so-called uncoupling protein, which can stimulate oxidative phosphorylation and thereby increase the metabolic rate (Peter Arner, The β3-Adrenergic Receptor—A Cause and Cure of Obesity? The New England Journal of Medicine, 333: p 382-383). The role of brown adipose tissue is to oxidize lipids to produce heat and rid the body of excess fat. White adipose tissue, which includes subcutaneous and visceral adipose tissue, is much more abundant. It serves to store fat, which can be mobilized by lipolysis to generate free fatty acids for use by other tissues.

Selective agonists of $β_3$-adrenergic receptors are potentially useful in treating obesity because they could enhance energy expenditure with few $β_1$- or $β_2$-adrenergic side effects. A number of $β_3$-adrenergic agonists have been developed and tested experimentally. Hence the treatment with β3-selective agonists can markedly increase energy expenditure and decreases body weight and obesity.

There are a few therapeutic interventions based on pharmaceutical drugs, such as phentermine (Fastin, Adipex P), for weight control but these methods exhibit side effects like high blood pressure, headache, insomnia, irritability and nervousness. The other important drug therapy for weight control is Xenical (Roche Pharm. Co. Ltd., Swiss), Reductil (Abbot Co. Ltd., USA). The most common side effects are gas, cramps and diarrhea, elevated blood pressure. All these therapies are based on active ingredients that are of synthetic origin. Effective anti-obese therapies with satisfactory efficacy and acceptable safety have not been developed so far.

More importantly, anti-obese agents of natural origin with proven safety are of great demand to control this growing menace. It is particularly advantageous for inhibition, amelioration and prevention of obesity if an anti-obesity action can be imparted to food products and beverages, which are ordinarily ingested.

Hence, presently there is great demand for development of agents for prevention, maintenance and remedy of obesity, which are safe and effective. The major emphasis now for many organizations around the globe has been to develop new dietary ingredients and compositions especially from natural origin.

*Holoptelea integrifolia* is a tall tree distributed through out India, but more densely in Gujarat, Madhya Pradesh, Hardwar and in the Himalayas. It belong to Ulmaceae family and is known by many local names, but more popularly as Kanju, Papri, nemali etc. *Holoptelea integrifolia* seed oil is a good source of edible oil. Its leaves are commonly used along with a blend of other Ayurvedic herbs in herbal tea preparations for detoxification and rejuvenation. This herbal tea is also known to clear cellulite deposits and obliterates stretch marks that are fall out of a weight problem. *Holoptelea integrifolia* was shown to exhibit antiviral activity in vitro assays. It was recognized as one of the plant species useful to control air pollution.

However, none of the prior art reported or disclosed the application of the extracts of *Holoptelea integrifolia* plant or purified fractions developed therefrom for the amelioration of adipogenesis and lipolysis or the prevention or treatment or maintenance adipogenesis and/or lipolysis mediated disorders such as obesity.

OBJECTS OF THE PRESENT INVENTION

The main object of the present invention is to provide pharmaceutical and nutraceutical compositions comprising the extracts or purified fraction of *Holoptelea integrifolia*, useful for the inhibition of obesity, and adipogenesis and lipolysis mediated diseases.

Another object of the present invention is to provide the process for the extraction of the dried plant parts of *Holoptelea integrifolia* using water and polar and non-polar organic solvents alone or mixture thereof.

A further object of the present invention is to provide an anti-adipogenic and pro-lipolytic composition containing the *Holoptelea integrifolia* ingredient capable of reducing body weight, total serum cholesterol level, phospholipids and triglycerides.

Yet another object of the invention is to provide a process for the preparation of a dietary, nutraceutical and pharmaceutical compositions, useful for the treatment of hyperlipedemia, obesity, lipogenic diabetes and atherosclerosis, which helps in keeping slim.

Still another object of the present invention is to provide herbal formulation(s) in combination with other anti-adipogenic plant extracts or powders useful in lowering lipids and for the treatment of atherosclerosis.

SUMMARY OF THE INVENTION

The present invention discloses herbal anti-adipogenic and pro-lipolytic supplement comprising a biologically effective amount of an extract or fraction derived from *Holoptelea integrifolia* (hereinafter referred merely to as "*Holoptelea* extract") as an active ingredient alone or compositions thereof. The compositions disclosed by the invention comprises of the said *Holoptelea* extract and optionally in combination with one or more known anti-obesic extracts and powders, along with biologically acceptable carrier or diluents.

In accordance to the present invention, dried plant parts, including leaf, seed, trunk and roots of *Holoptelea integrifolia* are repeatedly extracted with water or with polar or non polar organic solvents, alone or in combination. The extracts are combined, filtered, concentrated and then subjected to purification.

In one aspect, the purified extract of *Holoptelea integrifolia* comprising the active ingredient is formulated into a solid, semi-solid or liquid dosage form suitable for oral and parenteral administration alone or in combination with one or more anti-adipogenic or anti-obesic agents.

In another aspect, the purified extract of *Holoptelea integrifolia* are formulated into nutraceuticals and dietary supplements including food and beverages.

The anti-adipogenic and ptolipolytic composition comprising the extract or purified fractions of *Holoptelea integrifolia* of the present invention is effective for inhibition, amelioration or prevention of various diseases caused by uncontrolled adipogenesis and lipolysis thereof, for example, obesity, over weight, lipid storage disease, hyperlipedemia, atherosclerosis, thrombosis and hypercholesterolemia.

DESCRIPTION OF THE FIGURES

FIG. I presents the change in mean weight gain at weekly time intervals in the treatment groups supplemented with

*Holoptelea integrifolia* extract and positive control and control group of animals during the study of the protective effect against diet induced obesity.

Figure 1:
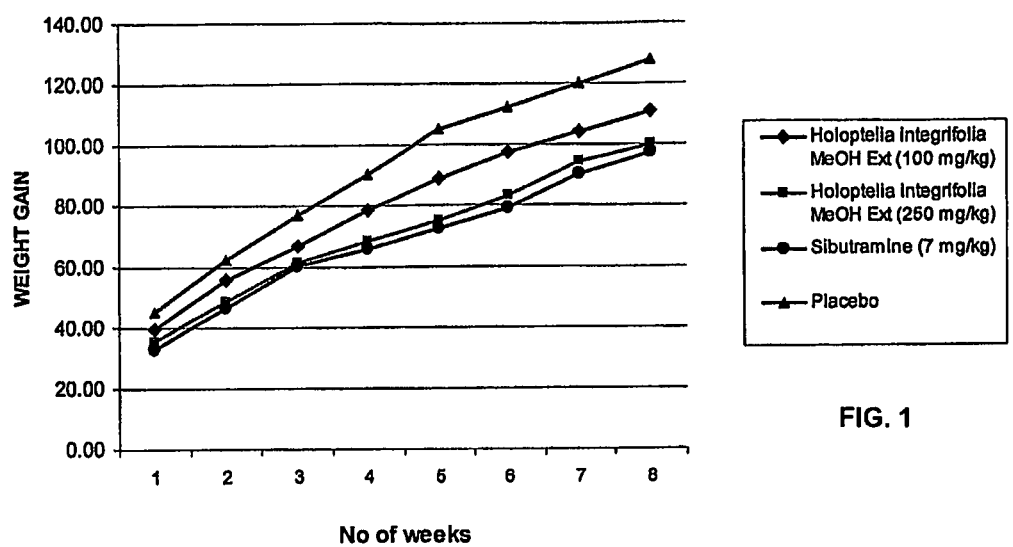
Figure 2:
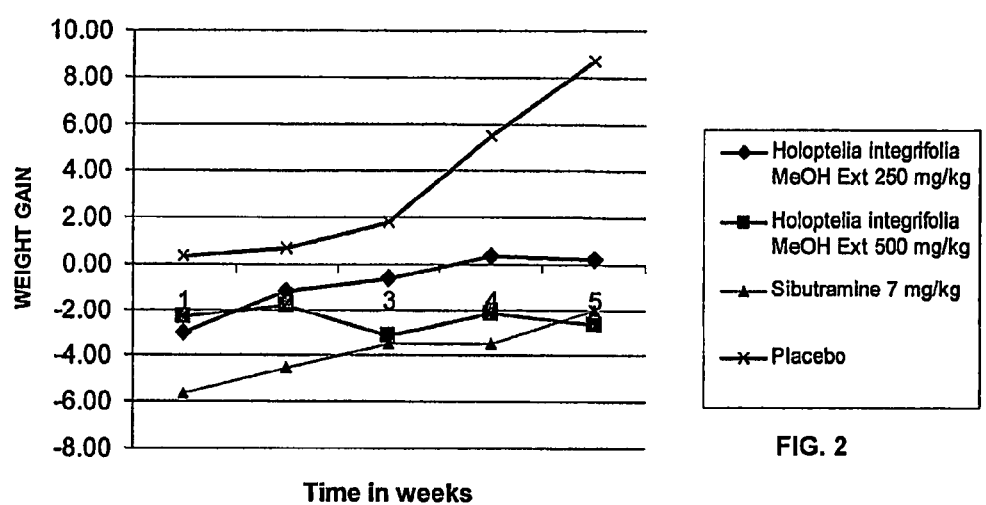

FIG. II presents the change in mean weight gain at weekly time intervals in the treatment groups supplemented with *Holoptelea integrifolia* extract and positive control and control group of animals during the study of the therapeutic effect against diet induced obesity.

DETAILED DESCRIPTION OF THE INVENTION

In the adipogenesis process, proliferation of preadipocytes needs to be followed by the differentiation of these cells to the mature adipocyte phenotype. Increased lipid accumulation in the mature adipocyte cells is the most important feature of this maturation process.

The uncontrolled fat accumulation in the body during the metabolic process is predominantly driven by the following key events. 1). Over expression and increase in the activity of protein tyrosine phosphatase 1B (PTB 1B) during the differentiation process of preadipocytes to mature adipocytes, 2). Highly increased lipid accumulation in the differentiated mature adipocytes. 3). Over expression and increased activity of Peroxisome Proliferator-Activated Receptor-gamma (PPAR-γ), a ligand activated nuclear receptor that acts as a lipid sensor, integrating the homeostatic control of energy, lipid, and glucose metabolism.

The breakdown of this fat in fat cells into glycerol and fatty acids is known as lipolysis. The body's adrenergic system plays a major part in regulating energy expenditure and lipolysis. Tightly regulated balance between lipid synthesis (adipogenesis or lipogenesis) and lipid mobilization (lipolysis) adjusts the fat storage level within cells.

Based on the above information, inventors of the present invention have undertaken screening of many herbal extracts using in vitro cell based assay and found unexpectedly that the extracts and purified fraction of *Holoptelea integrifolia* exhibit potent anti-adipogenic and pro-lipolytic activity. These in vitro results are further corroborated by in vivo experiments on diet induced obese animals. The *Holoptelea integrifolia* extracts conferred protection against weight gain in animals on fat rich diet. Supplementing the diet induced obese animals with *Holoptelea integrifolia* extract inhibited weight gain compared to the placebo group of animals.

The part of the plant to be extracted of *Holoptelea integrifolia* is not specifically limited, but includes, for example, leaf, seed, trunk, and root, preferably leaf. The plant parts to be extracted also referred to as raw material, are subjected to drying, for example, sun drying, shade drying, freeze drying and the like.

Accordingly, the process for the preparation of anti-adipogenic and pro-lipolytic herbal supplements containing *Holoptelea integrifolia* extract or fraction comprises the steps of:
  a) extracting the dried *Holoptelea integrifolia* plant parts with the water or organic solvent or mixtures thereof;
  b) filtering the extract through fine filters;
  c) evaporating the said filtrate to remove solvent to obtain the concentrated extract,
  d) purifying the concentrate to obtain active fraction and
  e) optionally mixing the extract or purified fraction with a known anti-obesic agent or antioxidant or bio-enhancer in a blender to obtain the composition.

The extraction of the plant material of the present invention is preferably carried out while gently stirring or allowing to stand using an extraction solvent in an amount preferably about 500 ml to 1 lit per 100 g of the extracting raw material. The extracting process is repeated at least twice. It is convenient in view of operability that the extraction temperature is in a range from room temperature to not higher than the boiling point of the solvent under normal pressure, and the extraction time for each cycle varies depending on the extraction temperature and the like.

The extraction solvent is selected from water or organic solvents including polar organic solvents and non-polar organic solvents or the mixture thereof.

Examples of the polar organic solvents include, but not limited to, lower alcohols having 1 to 4 carbon atoms such as methanol, ethanol, propanol, isopropanol, n-butanol, isobutanol, tert-butanol and the like, and ketones such as dimethyl ketone, methyl ethyl ketone, methyl isobutyl ketone and the like;

Examples of the non-polar organic solvents include, but not limited to, hexane, methyl acetate, ethyl acetate, butyl acetate, diethyl ether and the like.

The extraction method employed in the present invention is selected from immersion extraction, cold homogenizing extraction, heat extraction, continuous extraction, super critical extraction and the like.

The ratio of raw material to extraction solvent expressed as the ratio of dried *Holoptelea integrifolia*: solvent, is preferably about 1/100 to 1/2 (w/v), more preferably about 1/10 to 1/5 (w/v).

The extraction time for each cycle is in the range from 15 minutes to about 48 hours, preferably from about 30 minutes to 24 hours.

The extracts are combined and subjected to fine filtration to remove extraction residues by methods known per se such as filtration, centrifugation and the like, to obtain an extract. The solvent is removed from the extract by a method known per se, for example, thermal drying, freeze drying, evaporation under vacuum, freeze drying and the like to obtain a concentrated extract. A concentrated extract or a solution obtained by dissolving the concentrate in water and/or organic solvent which may be further purified by a method such as, for example, ultrafiltration, liquid-liquid extraction, adsorption resin treatment, size exclusion chromatography, partition chromatography, and the like. The active ingredient may be further purified by using adsorption chromatography, partition chromatography or ion-exchange chromatography and may be still further purified by a conventional procedure. The extract or purified fractions can be used for the present invention.

The extract or the fractions of *Holoptelea integrifolia* thus obtained, according to the present invention, is useful as a adipogenesis inhibitor and lipolysis accelerator as these products has exhibited strong anti-adipogenic and pro-lipolytic activities in cell based assays.

To obtain full benefit, it is preferable that the above-mentioned extract or purified substance is used as it is, or the active ingredient is formulated into a solid, semi-solid or liquid dosage form by adding a conventional biologically acceptable carrier or diluent.

Specific dosage form includes, for example, oral agents such as tablets, soft capsule, hard capsule, pills, granules, powders, emulsions, suspensions, syrups, and pellets; and parenteral agents such as injections, drops, suppositories and the like.

The *Holoptelea integrifolia* extracts or fractions may be optionally combined with one or more of known anti-adipogenic or anti-obese extracts or powders, specifically *Garcinia combogia*, green tea, green coffee bean, eucalyptus plant extract, double salt of (−)-hydroxycitric acid from

*Garcinia* species, *Gymnema sylvestre* extract, Banaba extract, carnitine, *Phaseolus vulgaris* extract, bitter orange (*Citrus aurantium*) extract, Chitosan, Conjugated linoleic acid, Glucomannan (Konjac plant extract), Green coffee bean extract, Caralluma extract, Sea weed extract, *Hoodia Gordonii* extract, *Commiphora mukul* gum resin extract, *Zingiber officinalis* extract, *Allium sativa* extract, chromium (III) complexes, DHEA, 7-KetoDHEA, and the composition obtained thereof is administered using a method described above.

The anti-adipogenic and/or pro-lipolytic compositions of *Holoptelea integrifolia* extracts or fractions, further comprise effective amounts of pharmaceutically or nutritionally or dietetically acceptable antioxidant(s), adaptogen(s), anti-inflammatory agents, anti-diabetic agent, bio-protectants, bio-availability enhancers and trace metals or mixtures thereof to form a formulation.

The anti-adipogenic and pro-lipolytic formulations in the present invention is prepared by formulating the extracts or purified fractions of *Holoptelea integrifolia*, or compositions thereof along with the biologically acceptable carrier or diluents.

The examples of the biologically acceptable carrier or diluents employed in the present invention includes, but are not limited to, surfactants, excipients, binders, disintegrators, lubricants, preservatives, stabilizers, buffers, suspensions and drug delivery systems.

Preferred examples of solid carriers include, glucose, fructose, sucrose, maltose, sorbitol, stevioside, corn syrup, lactose, citric acid, tartaric acid, malic acid, succinic acid, lactic acid, L-ascorbic acid, dl-.alpha.-tocopherol, glycerin, propylene glycol, glycerin fatty ester, polyglycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, and preservatives.

Preferred examples of liquid carriers (diluents) include, distilled water, saline, aqueous glucose solution, alcohol (e.g. ethanol), propylene glycol, and polyethylene glycol; and oily carriers such as various animal and vegetable oils, white soft paraffin, paraffin, and wax.

In alternative aspect of the invention, the product of the present invention is delivered in the form of controlled release tablets, using controlled release polymer-based coatings by the techniques known in the art. The said formulation is designed for once a daily administration.

In accordance to the present invention, the *Holoptelea integrifolia* extracts or fractions is formulated into any food and drink forms such as solid food like chocolate or nutritional bars, semisolid food like cream or jam, or gel. Contemplation was also done to formulate the product of the invention into a beverage and the like, such as refreshing beverage, coffee, tea, milk-contained beverage, lactic acid bacteria beverage, drop, candy, chewing gum, chocolate, gummy candy, yoghurt, ice cream, pudding, soft adzuki-bean jelly, jelly, cookie and the like. These various preparations or foods and drinks are useful as a healthy food for the treatment and/or prevention of obesity.

The method of treatment teaches that the amount of the *Holoptelea integrifolia* extract or purified fraction to be administered or ingested to mammals in the form of above-mentioned nutraceutical and dietary compositions may not be uniform and varies depending on the nature of the formulation and suggested human or animal dosage of the extract or the fractions, but preferably within a range from 0.01 to 300 mg/kg weight/day.

The quantity of the extract or the purified fraction in the above-mentioned various foods and beverage compositions may also not be uniform and varies depending on the nature of the formulation and suggested human or animal dosage of the extract or the fractions, for example, about 0.0001 to 50 wt %, preferably about 0.001 to 20 wt %, more preferably about 0.01 to 10 wt %.

The supplementation of *Holoptelea integrifolia* extract or purified fraction in the composition of the present invention contains about 1%-100% by weight of the above extract based on the total weight of the composition.

The health care food of the present invention comprises the above extract up to 0.1 to 80%, preferably 1 to 50% by weight based on the total weight of the composition.

The animal feed in the present invention is prepared by mixing the *Holoptelea integrifolia* extract or fractions with various components used in the animal feed for the purpose of inhibition, amelioration or prevention of obesity, lipid storage disease, hyperlipedemia, cardiovascular disease, artherosclerosis and thrombosis, or for the purpose of inhibition or reduction of an amount of triglyceride or an amount of cholesterol in blood, inhibiting or preventing obesity.

The form of the food additive for animal feed is not specifically limited and the *Holoptelea integrifolia* extract may be added to food products as it is, or as a composition, to various cooked and processed food products. The quantity may be the same as that used in case of food products. Similarly, the ingredients may also be added during or after preparation of the animal feeds.

The invention also describes a method of treating obesity and, adipogenesis and lipolysis involved diseases in mammals comprising administering to a mammal in need a therapeutically effective amount of *Holoptelea integrifolia* extract or purified fraction or compositions thereof.

The mammal is a human or an animal. The route of administration can be topical or oral or parenteral.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Dried leaves of the plant material *Holoptelea integrifolia* (1 Kg) was pulverized to coarse powder, extracted with methyl alcohol (5 L) at room temperature (RT) for 1 hr. Extraction process was repeated thrice using methyl alcohol (3 L+3 L+2 L). All the extracts were combined and the combined alcoholic extracts were fine filtered, and the clear extract was evaporated to dryness on a climbing film evaporator at 50-60° C. under vacuum to obtain the residue (80 g)

Example 2

Dried leaves of the plant material *Holoptelea integrifolia* (1 Kg) was pulverized to coarse powder, extracted with water/methyl alcohol (40:60; 6 L) at RT for 1 hr. Extraction process was repeated three times using hydroalcohol 40/60 (5 L+3 L+3 L). All the water/methyl alcohol extracts were combined, subjected to fine filtration, and the clear extract was evaporated to dryness on a climbing film evaporator at 50-60° C. under vacuum to obtain the residue (100 g).

Example 3

Dried leaves of the plant material *Holoptelea integrifolia* (1 Kg) was pulverized to coarse powder, extracted with water (6 L) at RT for 1 hr. Extraction process was repeated three times using water (4 L+4 L+2 L). All the extracts were combined, the combined aqueous extracts were fine filtered, and the clear extract was evaporated to dryness on a climbing film evaporator at 50-60° C. under vacuum to obtain the residue (105 g).

Example 4

The *Holoptelea integrifolia* methanol extract (50 g) was dissolved in 30% methanol (1 L) and eluted through R-20 resin column (550 mL, synthetic adsorbent) and the column washed with water (1 L). The resin was then eluted with 80% methanol (1 L). The fractions eluted with 80% methanol were combined and the solvent evaporated under reduced pressure to give the bio-enriched fraction of *Holoptelea integrifolia* extract (23 g).

Example 5

Assessment of Inhibition of Lipid Accumulation in Differentiated Adipocytes by *Holoptelea integrifolia* Extract:

One hundred thousand 3T3-L1 Human pre-adipocyte cells in Dulbecco's Modified Eagles Medium (DMEM) containing 10% Fetal Bovine Serum (FBS) were taken into each well of a 24-well plate and incubated for 48 h at 37° C. and 5% $CO_2$. The differentiation of pre-adipocyte cells was initiated in a differentiation medium containing 10 µg/ml insulin, 1.0 µM dexamethasone, and 0.5 mM isobutylmethylxanthine (IBMX) for 48 h. After this the medium was replaced by DMEM containing 10 ug/ml insulin and incubated for 3 days. Then the differentiating cells were treated with 10 µg/ml of *Holoptelea integrifolia* hydroalcohol (60% methanol) extract or methanol extract or bio-enriched fraction separately and maintained in the medium for another 3-5 days. The cells incubated with 0.1% DMSO were considered as the vehicle control. After the incubation period, cells were washed with phosphate buffered saline (PBS) and fixed with 10% buffered formalin for 1 h at room temperature. One small aliquot of cell suspension was separated for cell counting in hemocytometer chamber. Fixed cells were stained with Oil Red O solution to measure the cellular neutral lipid accumulation. Briefly, cells were washed with PBS, fixed with 10% buffered formalin and stained with Oil Red O solution (0.5 g in 100 ml isopropanol) for 10 min. After removing the staining solution, the dye retained in the cells will be eluted into isopropanol and OD measured at 550 nm. The inhibition of fat accumulation in the treated cells was compared with the mock treated differentiated adipocytes. The treated and control cells were also analyzed and compared for inhibition of lipid accumulation visually under microscope and recorded digitally in suitable image capture system. The *Holoptelea integrifolia* methanol and 60% methanol extracts and bio-enriched fraction showed 46%, 45% and 55% inhibition of lipid accumulation respectively.

Example 6

Assessment of Pro-Lipolytic Activity of *Holoptelea integrifolia* Extract in Differentiated Adipocytes:

The lipolytic activity was assessed in mature adipocytes as per the procedure of Chemicon International, USA, by measuring free glycerol secreted into the culture medium. The 3T3-L1 cells were differentiated for 5 days and then the culture medium was removed. The monolayer was washed twice with wash solution (Hank's balanced salt solution), and then 250 µL of incubation solution (Hank's balanced salt solution plus 2% bovine serum albumin) was added to the wells in triplicate in presence and absence of *Holoptelea integrifolia* methanol extract, and the cells were further incubated for 16 h. To measure lipolysis, 200 µL of free glycerol assay reagent was added to 25 µL of culture supernatants and controls containing glycerol standard. The samples and the controls were incubated for 15 min, and the absorbance was read at 540 nm. A standard curve constructed from the glycerol standard was used to calculate the concentration of free glycerol in the culture supernatants. The percentage increase in glycerol concentration in the sample solutions compared to the control containing the known concentrations of glycerol corresponds to the percentage acceleration of lipolysis by *Holoptelea integrifolia* extracts. The percentage increase in lipolysis accelerated by *Holoptelea integrifolia* methanol extract is 70.2%.

Example 7

Protective Effect of *Holoptelea integrifolia* Against Diet Induced Obesity in Rats.

Selected healthy Sprague-Dawley rats were randomly assigned to control or various treatment groups (n=6). All the animals allocated for protective phase of the study were on dietary intervention by feeding high fat diet ad libitum and the animals allocated to treatment groups were simultaneously given oral administration of 100 mg or 250 mg/kg *Holoptelea integrifolia* methanol extract in 10 mL of 0.5% CMC, using gastric tube for the entire 8 week study duration. The test animals of the control group were simultaneously given 10 ml/kg of 0.5% CMC. Sibutramine (7 mg/kg body weight) was used as a positive control. Food and water consumption were recorded daily, body weights were recorded weekly and fasting blood samples were collected before initiation, after $4^{th}$ week and $8^{th}$ week (termination) of the study. The weight gain is plotted against the study duration in weeks (FIG. I). The treatment groups corresponding to 100 mg/kg and 250 mg/kg doses showed 15.4% and 27.3% protection respectively against weight gain, in diet induced obesity, when compared with untreated control group. Sibutramine exhibited 30.5% reduction in weight gain compared to the control group. The animals of the treatment group also showed significant reduction in serum triglycerides and lipid profile (anti-hyperlipidimic activity). Upon administration of *Holoptelea integrifolia* alcohol extract for a period of 60 days, the level of triglyceride in the obese rats was reduced by 50% compared to the control. The levels of serum cholesterol and LDL were reduced by 40% and 45% respectively, whereas the level of HDL was increased by 25%.

Example 8

Anti-Obese Activity of *Holoptelea integrifolia* in Diet Induced Obese Rats.

Selected healthy Sprague-Dawley rats were randomly assigned to control or various treatment groups (n=6). All the animals allocated for the study were made obese through dietary intervention by feeding high fat diet ad libitum for 8 weeks. After 8 weeks, the treatment group of animals was given oral administration of 250 mg/kg or 500 mg/kg of *Holoptelea integrifolia* alcohol extract in 10 mL of 0.5% CMC, using gastric tube for 5 week study duration. Sibutramine (7 mg/kg body weight) is used as a positive control. The control group of animals were given 10 ml/kg of 0.5% CMC. Food and water consumption were recorded daily, body weights were recorded weekly and fasting blood samples were collected before initiation after 5$^{th}$ week of the study. The weight gain for different groups compared at weekly intervals (FIG. II). The reduction in body weight gain of animals in treatment groups corresponding to 250 mg/kg and 500 mg/kg doses are about 98.1% and 130.8% respectively compared to those in the untreated control group. Sibutramine exhibited 123.1% reduction in weight gain compared to the control group. The treatment group of animals also showed significant reduction in serum triglycerides and lipid profile (anti-hyperlipidemic activity) when compared to the control group.

A review of foregoing sequence of experimental protocols shows that an extract of *Holoptelea integrifolia* has an excellent action of inhibiting adipogenesis, accelerating lipolysis and reducing body weight.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

We claim:

1. A dosage form comprising an anti-adipogenic or pro-lipolytic composition, wherein said composition comprises an herbal supplement consisting of:
    a) an effective amount of an alcohol extract of *Holoptelea integiffblea*; and
    b) an effective amount of an antiobesic agent; wherein said extract is obtained by:
        i) extracting *Holoptelea integrifolia* leaves with an alcoholic solvent, wherein said alcoholic solvent, optionally, contains up to 40% water to provide a solution;
        ii) filtering said solution to obtain a clear filtrate; and
        iii) evaporating the clear filtrate to dryness to provide the extract of *Holoptelea integrifolia*; and
    wherein said dosage form is selected from the group consisting of a tablet, a capsule, a pill, a suppository, and a controlled release tablet.

2. The dosage form of claim 1, wherein said effective amount of said extract of *Holoptelea integrifolea* is between 1% and 50% by weight of said herbal supplement.

3. The dosage form of claim 1, wherein said dosage form further comprises a biologically acceptable excipient.

4. The dosage form of claim 3, wherein the dosage form is for oral administration.

5. The dosage form of claim 3, wherein said dosage form is parenterally administered, and is a suppository.

6. The dosage form of claim 1, wherein the composition: optionally, further comprises an antioxidant or a bio-enhancer.

7. The dosage form of claim 1, wherein the antiobesic agent is selected from the group consisting of: extracts or powders of *Garcinia cambogia*, green tea, green coffee bean, eucalyptus plant extract, a double salt of (-)-hydroxycitric acid derived from *Garcinia* species, *Gymnema sylvestre* extract, Banaba extract, carnitine, *Phaseolus vulgaris* extract, bitter orange (*Citrus aurantium*) extract, chitosan, conjugated linoleic acid, glucomannan (Konjac plant extract), green coffee bean extract, Caralluma extract, *Hoodia Gordonii* extract, *Commiphora mukul* gum resin extract, *Zingiber officinalis* extract, *Allium sativa* extract, chromium (III) complexes, DHEA, 7-Keto-DHEA, and mixtures thereof.

8. A method for treating obesity or hyperlipedemia in a patient in need thereof comprising:
    administering an effective amount of the dosage form of claim 1 to said patient, wherein the dosage form is an oral dosage form or a parenteral dosage form.

9. A method for lowering plasma triglycerides in a patient, comprising:
    administering an effective amount of the dosage form of claim 1 to said patient, wherein the dosage form is administered as an oral dosage form or a parenteral dosage form.

10. The dosage form of claim 1, wherein said composition further comprises an effective amount of at least one pharmaceutically or nutritionally or dietetically acceptable antioxidant, adaptogen, anti-inflammatory agent, anti-diabetic agent, bio-protectant, bioavailability enhancer, trace metal, or mixture thereof.

11. The dosage form of claim 1, wherein said effective amount of said extract of *Holoptelea integrifolea* is between 0.1% and 80% by weight of said herbal supplement.

12. The dosage form of claim 1, wherein said effective amount of said extract of *Holoptelea integrifolea* ranges between 0.1% and 20% by weight of said herbal supplement.

13. A dosage form comprising an anti-adipogenic and pro-lipolytic composition, said composition comprising: an alcohol extract of *Holoptelea integrifolea* in an amount between 1% and 50% by weight of the composition;
    at least one biologically acceptable excipient; and
    an antiobesic agent; wherein
    said extract of *Holoptelea integrifolea* is obtained by extracting *Holoptelea integrifolea* leaves with alcoholic solvent, said alcoholic solvent optionally containing up to 40% water; wherein
    said composition:
        a) inhibits adipogenesis in mammals;
        b) promotes lipolysis in mammals; or
        c) inhibits adipogenesis and promotes lipolysis in mammals; and wherein
    said dosage form is in the form selected from the group consisting of: a tablet, a capsule, a pill, a suppository, and a controlled release tablet.

14. The dosage form of claim 1, wherein said effective amount of said extract of *Holoptelea integrifolea* is between 0.1% and 10% by weight of said herbal supplement.

15. A dosage form comprising an anti-adipogenic and pro-lipolytic composition effective for inhibiting or controlling obesity, overweight, or hyperlipidemia in mammals, wherein
    said composition comprises:
        i) from 0.1% to 80% by weight of an alcohol extract of *Holoptelea integrifolia*, wherein said extract of *Holoptelea integrifolia* is obtained by extracting *Holoptelea integrifolia* leaves with an alcoholic solvent, said alcoholic solvent optionally containing up to 40% water; and
        ii) an effective amount of at least one antiobesic agent;
    and wherein said dosage form is in the form selected from the group consisting of: a tablet, a capsule, a pill, a suppository, and a controlled disease tablet.

16. A dosage form comprising an anti-adipogenic or pro-lipolytic composition, said composition comprising an herbal supplement, wherein said herbal supplement comprises an effective amount of an alcohol extract of *Holoptelea integrifolea* wherein said extract of *Holoptelea integrifolea* is a bioenriched extract and is obtained by:
a) extracting *Holoptelea integrifolea* leaves with an alcoholic solvent, said alcoholic solvent optionally containing up to 40% water, to produce a first extract;
b) loading said first extract onto a chromatography column containing an R-20 resin;
c) washing said chromatography column with water;
d) eluting said column with a second polar organic solvent to produce an eluate; and
e) evaporating said second polar organic solvent from the eluate to produce said bioenriched extract; and wherein said dosage form is selected from the group consisting of a tablet, a capsule, a pill, a suppository, and a controlled release tablet.

* * * * *